United States Patent [19]

Williams, Jr.

[11] 4,412,080

[45] Oct. 25, 1983

[54] METHODS FOR PREPARING CYCLOPOLYSILOXANES

[75] Inventor: Robert E. Williams, Jr., Scotia, N.Y.

[73] Assignee: General Electric Company, Schenectady, N.Y.

[21] Appl. No.: 408,103

[22] Filed: Aug. 16, 1982

[51] Int. Cl.$^3$ ............................................... C07F 7/08
[52] U.S. Cl. ................................................... 556/460
[58] Field of Search ......................................... 556/460

[56] References Cited

U.S. PATENT DOCUMENTS

| | | | |
|---|---|---|---|
| 2,860,152 | 11/1958 | Fletcher | 556/460 |
| 3,398,173 | 8/1968 | Goossens | 556/460 X |
| 3,590,064 | 6/1971 | Lacefield | 556/460 X |
| 3,763,212 | 10/1973 | McEntee et al. | 556/460 |
| 3,983,148 | 9/1976 | Reedy et al. | 556/460 |
| 4,276,425 | 6/1981 | Burkhardt et al. | 556/460 |

*Primary Examiner*—Paul F. Shaver
*Attorney, Agent, or Firm*—William H. Pittman; James C. Davis, Jr.; James Magee, Jr.

[57] ABSTRACT

Cyclic methyl polysiloxanes can be prepared by hydrolysis of dimethyldichlorosilane and aqueous hydrochloric acid in the presence of a normal $C_{6-16}$ alkyl sulfonic acid to give good yields of cyclic polysiloxanes and minimal amounts of linear silanols.

8 Claims, No Drawings

METHODS FOR PREPARING CYCLOPOLYSILOXANES

BACKGROUND OF THE INVENTION

This invention relates to an improved method for hydrolyzing and condensing dimethyldichlorosilane so as to prepare a cyclic siloxane of the general formula:

$$[(CH_3)_2SiO]_m \qquad \text{I}$$

where m is a whole number predominantly ranging from 3-6, inclusive. This preparation of cyclic polysiloxanes is accomplished by hydrolyzing dimethyldichlorosilane in the presence of a normal $C_{6-16}$ alkyl sulfonic acid having the formula:

$$n\text{-}C_xH_{2x+1}SO_3H \qquad \text{II}$$

where $x = 6$ to 16, inclusive.

The term "normal $C_{6-16}$ alkylsulfonic acid" is intended to include not only the acid itself but also its negatively charged alkali metal salts thereof, for instance, the sodium salt of the sulfonic acid. For convenience, availability, and cost, the sodium salt (which is an anionic surfactant while the corresponding free sulfonic acids are nonionic surfactants) is used in the examples which are illustrative of this invention. However, essentially all the sodium salts are analogues of the sulfonic acids and are converted to the acid in the presence of the aqueous HCl, which is used for hydrolysis purposes. Therefore, the active catalyst is the alkyl sulfonic acid, or mixtures thereof.

Among the n-alkyl sulfonic acids which can be employed in the practice of the present invention, in addition to those recited in the following examples, may be mentioned for instance, $C_{10}H_{21}SO_3H$, $C_{12}H_{25}SO_3H$, $C_{14}H_{29}SO_3H$, $C_{16}H_{33}SO_3H$, etc. Included within the scope of these sulfonic acids are the precursor alkali-metal salts thereof, such as the sodium, potassium, etc. salts, which under the reaction conditions of carrying out the invention, are converted to the sulfonic acid.

By means of this invention, the dimethyldichlorosilane when hydrolyzed gives a number of cyclic polysiloxanes according to formula I which predominantly are of the type where m is 3-6 with a minimum of linear dimethylsiloxanes terminated with silanol groups.

STATEMENT OF THE INVENTION

Cyclic polysiloxanes, particularly cyclic dimethyl siloxanes, such as those in formula I where m is 4 (also called "tetramer") or m is 5 (also called "pentamer"), or even where m is 6 (also called "hexamer") are extremely desirable in the silicone art. Even the lowest cyclic polysiloxane where m is 3 (also called "trimer") has a value, but is usually formed in smaller amounts than either the tetramer or the pentamer.

These cyclic dimethylsiloxanes have many uses. From these cyclic polysiloxanes there may be prepared silicone rubbers, silicone fluids, including silicone lubricating oils, etc. These cyclics can be used by themselves for foam suppression in certain applications. The pentamer has been used in cosmetic applications, e.g., in anti-perspirant formulations.

It is commercially important that in preparing these polysiloxanes that they be in a cyclic form, since when making silicone gums, they can be readily purified and then used as the starting materials with alkali metal salts as condensing agents. Thus, the silicone gums are generally prepared by heating the cyclic tetramer with KOH to form the gum which in turn is filled with reinforcing fillers, such as fume silica, and then molded with a curing agent, such as benzoyl peroxide, to form heat-resistant silicone products.

In making silicone fluids, it is generally desirable to react a cyclic polysiloxane in the above category with hexamethyldisiloxane with a mineral acid so that linear polysiloxanes are formed with chain-stopped trimethylsiloxy units or any other organosiloxy units which it may be desired to insert or other chain-stoppers into the polymer chain.

PRIOR ART

It is known to hydrolyze dimethyldichlorosilane with water in the presence of a cationic surface active agent, where the surface active agent bears a positive charge rather than a negative charge, as is more particularly disclosed in Reedy et al U.S. Pat. No. 3,983,148 issued Sept. 28, 1976. Reedy et al have employed a wide range of cationic surfactants to enhance the yield of the cyclic polysiloxanes; but in their process the cationic surface active agent which is essentially soluble only in the aqueous phase is selected from a limited class of salts or protonated compounds. The use of the alkyl sulfonic acid has an advantage over the Reedy et al surfactant in that the sulfonic acid is less expensive and more readily available, particularly as the sodium salt. In Reedy et al, the surface active portion of the molecule bears a positive charge, while in my invention the surface active portion is neutral. Since sulfonic acids and their alkali metal salts are resistant to hydrolysis in the presence of hot acid or alkali, they have an advantage over Reedy et al's catalysts which are subject to acid catalyzed elimination reactions which form products that can dissolve in and contaminate the formed siloxanes.

Removal of residual HCl from the siloxanes is typically accomplished by stirring the siloxanes with an aqueous solution of sodium carbonate or sodium bicarbonate to effect neutralization of the HCl to NaCl. Subsequent phase separation yields siloxanes with very low chloride values, suitable for further processing. The protonated cationic surfactants claimed by Reedy et al. are predominately soluble in the aqueous hydrolysis medium. However, small amounts will be retained in the siloxane products and carried into the neutralization step. At this point these protonated cationic surfactants, like the residual HCl, will be neutralized by the aqueous base. The resulting neutral molecules, (e.g., amines, phosphines, alcohols, etc. disclosed by Reedy et al) will now be more soluble in the siloxane phase than in the aqueous phase and will remain as contaminants in the siloxane product. In contrast to protonated cationic surfactants, sulfonic acids of my invention are not neutralized by base treatment and remain totally soluble in the aqueous media.

The sulfonic acid is used only in small effective catalytic amounts required to give the desired results of obtaining predominantly large quantities of cyclic polysiloxane where m in formula I is 3-6. Even more advantageous is the fact that under the conditions in my invention, the cyclic polysiloxanes are predominantly of the more desirable tetramer or pentamer type, that is where m in formula I equals 4 or 5.

Thus, the amount of the sulfonic acid which can be employed varies from about 0.1% to about 2%, by weight, based on the weight of the aqueous HCl hydrolysis medium and depending on whether one wishes larger amounts of tetramer or pentamer. The longer alkyl chains of the sulfonic acid, although useful, form emulsions and may thereby complicate separation of the desired product.

The amount of water in the aqueous HCl which is used with the dimethyldichlorosilane can range from 2 to 30 moles or more of water per mole of silane and should be sufficient at least to hydrolyze all the silicon-bonded chlorine. Generally, I have found that using about 10 to 20 moles of water (in the aqueous HCl) per mole of dimethyldichlorosilane is sufficient to yield large amounts of cyclics of formula I. In addition, within these limitations as far as the amount of water which is used with the dimethyldichlorosilane is concerned, often there is a direct evolution of HCl (especially when using 36% HCl) resulting in recovery of anhydrous HCl from the hydrolysis reactor. The HCl concentration in the water should range from about 20% to 36% HCl or saturated aqueous HCl.

The temperature at which the reaction is carried out should be carefully monitored between 0° to 100° C., preferably between 30° to 90° C. The mean liquid residence time of the aqueous HCl and the chlorosilane while the hydrolysis reaction is taking place (advantageously with good mixing) is varied widely and is of the order of about 10 minutes to 1 hour, depending on whether the tetramer or pentamer is desired.

Surprisingly, I have found that by a variation of conditions, I can increase the amount of either tetramer or pentamer formation, For instance, in making the tetramer, the temperature of the reaction should be maintained at 50° C. or below while the concentration of the sulfonic acid catalyst can vary from about 0.25 to 2%, by weight, based on the weight of the aqueous HCl. Also, in order to increase the yeilds of tetramer, the time of reaction should be carefully monitored so that it is below 1 hour. When making the pentamer, however, the attainment of increased yields of this latter material is dependent upon such factors as the percent of catalyst used, and the length of the alkyl chain (which can be longer than when making tetramer), the temperature at which the reaction is carried out, and the length of time of reaction. In making the pentamer, I can use as low as 0.1% catalyst and as high as 2%. Also, the temperature advantageously is between 60°-100° C. in order to insure greater yields of the pentamer. Furthermore, the times of reaction when making increased yields of the pentamer are longer and may range from about ½ hour to as much as 12 hours.

It is thus evident from the above discussion that the use of the alkyl sulfonic acid provides a versatility for making increased yields of either the tetramer or the pentamer, depending upon the conditions used.

In order that those skilled in the art may better understand how the present invention may be practiced, the following examples are given by way of illustration and not by way of limitation. All parts are by weight, unless otherwise indicated.

In the following examples, the mode of reaction for making increased yields of tetramer was as follows: 129 grams dimethyldichlorosilane was added dropwise to 200 grams aqueous HCl, either 20% HCl or 36% HCl, by weight, with or without the catalyst over a period of 25 minutes at 35° C. in a constant temperature bath while stirring vigorously. After 5 minutes of additional stirring, the mixture was separated by gravity and the siloxane layer stirred with an equal volume of saturated aqueous sodium bicarbonate solution at 50°-70° C. for about 15-20 minutes to neutralize any residual amounts of HCl which might be present in the siloxane layer. The siloxane layer was again separated by gravity and analyzed by gas chromatography with n-nonane as the internal standard. The following Table I shows the results of effecting the reaction in the presence of the aqueous HCl at concentrations of 20% and 36% HCl as well as examples where the catalyst sulfonic acid was omitted in making the cyclic polysiloxane.

TABLE I

| Example No. | Surfactant | Sulfonic Acid Surfactants Wt Surfactant Based On Wt Aqueous Acid | Acid | $D_3$ | $D_4$ | $D_5$ | Total Cyclic |
|---|---|---|---|---|---|---|---|
| 1 | No Surfactant | | 20% HCl | — | 54% | 11% | 68% |
| 2 | No Surfactant | | 36% HCl | 1% | 41% | 12% | 57% |
| 3 | n-$C_6H_{13}SO_3^-Na^+$ | 0.5% | 36% HCl | — | 47% | 13% | 63% |
| 4 | n-$C_8H_{17}SO_3^-Na^+$ | 0.25% | 36% HCl | — | 56% | 15% | 75% |
| 5 | n-$C_8H_{17}SO_3^-Na^+$ | 0.50% | 36% HCl | — | 63% | 17% | 85% |
| 6 | n-$C_8H_{17}SO_3^-Na^+$ | 1.0% | 36% HCl | — | 55% | 24% | 83% |
| 7 | n-$C_8H_{17}SO_3^-Na^+$ | 2.0% | 36% HCl | 1% | 56% | 21% | 83% |
| 8 | n-$C_8H_{17}SO_3^-Na^+$ | 0.25% | 20% HCl | — | 60% | 15% | 79% |
| 9 | n-$C_8H_{17}SO_3^-Na^+$ | 0.5% | 20% HCl | — | 72% | 14% | 89% |
| 10 | n-$C_8H_{17}SO_3^-Na^+$ | 0.75% | 20% HCl | — | 69% | 15% | 87% |
| 11 | n-$C_8H_{17}SO_3^-Na^+$ | 1.0% | 20% HCl | — | 60% | 15% | 80% |

EXAMPLE 12

This example illustrates a means for increasing the yield of pentamer to a higher value than is normally obtained when carrying out the reaction previously described in making the tetramer. More particularly, 100 grams dimethyldichlorosilane was added dropwise over 20 minutes to 200 grams 20% HCl containing 1.0 gram of $C_{10}H_{21}SO_3^{(-)}Na^{(+)}$ at 45° C. During additions of the dimethyldichlorosilane, the temperature increased to 62° C. After 30 minutes total reaction time, a sample was removed and the reaction solution was heated to 90° C. The sample was analyzed by VPC (nonane as internal standard). Additional samples were taken at 1 hour and 1.5 hours reaction time. The following Table II shows the results of different tests which were conducted under the conditions herein described at periods of 0.5 hour and 1.5 hours and varying the temperature within the range of 60°-90° C.

TABLE II

| Reaction Time | % Tetramer | % Pentamer | % *Hexamer |
|---|---|---|---|
| 0.5 hour | 50% | 24% | 4% |
| 1.5 hours | 45% | 43% | 10% |

*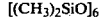

It will be noted that there are critical differences in time and temperature at which the reaction is carried out to obtain the increased yields of pentamer as compared to tetramer.

In this example, conditions similar to that described in Example 12 were used with the exception that the catalyst was $C_8H_{17}SO_3^{(-)}Na^{(+)}$ (2.0 grams), the time of reaction was 1 hour and the temperature at which the reaction was carried out was 60° C. The following Table III shows the results of carrying out this reaction under the above-identified conditions.

TABLE III

| Tetramer | Pentamer | Hexamer |
|---|---|---|
| 40% | 41% | 11% |

In this case, a stable emulsion was obtained which could be readily broken by means well known in the art to separate out and to determine the amounts of the various components listed in Table III.

It will of course be understood by those skilled in the art that other sulfonic acids and their alkali-metal salts as well as conditions for carrying out my invention can be varied widely, as is more particularly described previously, depending on whether one is interested in obtaining increased yields of the tetramer or the pentamer. Thus if one desires making increased yields of pentamer longer chain alkyl sulfonic acids can be employed; in addition higher temperatures and longer times of reaction of the ingredients tend toward making the increased yields of the pentamer. On the other hand, if the desire is to make larger yields of the tetramer, temperatures below 50° C. should be employed and shorter chain alkyl sulfonic acids, particularly the n-octyl sulfonic acid should be employed. In addition, in making higher yields of the tetramer, generally the less concentrated aqueous HCl solution is preferred.

What I claim and desire to secure by Letters Patent of the United States is:

1. A process for preparing cyclic dimethylsiloxanes of the formula:

$$[(CH_3)_2SiO]_m$$

where m predominantly equals a whole number from 3-6, which comprises hydrolyzing dimethyldichlorosilane with a normal $C_{6-16}$ alkylsulfonic acid with aqueous HCl containing, by weight, from 20% to saturated aqueous HCl depending on the temperature.

2. The process as in claim 1 wherein the reaction temperature is from 0°-100° C.

3. The process as in claim 1 wherein the sulfonic acid is present in an amount ranging from 0.1 to 2%, by weight, based on the weight of the aqueous HCl.

4. The process as in claim 1 wherein the water in the aqueous HCl to the dimethyldichlorosilane is in a molar ratio between 2 to 30 moles of the former per mole of the dimethyldichlorosilane.

5. The process for making octamethylcylcotetrasiloxane which comprises hydrolyzing dimethyldichlorosilane in the presence of a normal $C_{6-16}$ alkyl sulfonic acid, with from 20-36% aqueous HCl at a temperature below 50° C.

6. The process as in claim 5 wherein the alkyl sulfonic acid is n-octyl sulfonic acid.

7. The process for making decamethylcyclopentasiloxane which comprises hydrolyzing dimethyldichlorosilane in the presence of a normal $C_{6-16}$ alkyl sulfonic acid with aqueous HCl containing by weight 20-36% HCl at a temperature in excess of 50° C. and for a time greater than 0.5 hour.

8. The process as in claim 7 wherein the alkyl sulfonic acid is $C_{10}H_{21}SO_3H$.

* * * * *

UNITED STATES PATENT AND TRADEMARK OFFICE
CERTIFICATE OF CORRECTION

PATENT NO. : 4,412,080

DATED : October 25, 1983

INVENTOR(S) : Robert E. Williams, Jr.

It is certified that error appears in the above-identified patent and that said Letters Patent is hereby corrected as shown below:

Column 2, line 55, cancel "not"

Signed and Sealed this

Thirteenth Day of March 1984

[SEAL]

Attest:

GERALD J. MOSSINGHOFF

Attesting Officer

Commissioner of Patents and Trademarks